United States Patent
Chan et al.

(10) Patent No.: US 8,326,415 B2
(45) Date of Patent: Dec. 4, 2012

(54) SYSTEM FOR ALTERING MOTIONAL RESPONSE TO SENSORY INPUT

(75) Inventors: Alistair K. Chan, Bainbridge Island, WA (US); Roderick A. Hyde, Redmond, WA (US); Jordin T. Kare, Seattle, WA (US); Lowell L. Wood, Jr., Bellevue, WA (US)

(73) Assignee: The Invention Science Fund / LLC

( * ) Notice: Subject to any disclaimer, the term of this patent is extended or adjusted under 35 U.S.C. 154(b) by 243 days.

(21) Appl. No.: 12/290,663

(22) Filed: Oct. 31, 2008

(65) Prior Publication Data

US 2010/0114255 A1   May 6, 2010

(51) Int. Cl.
| *A61N 1/00* | (2006.01) |
| *A61B 5/00* | (2006.01) |
| *A61B 5/103* | (2006.01) |
| *A61B 5/12* | (2006.01) |

(52) U.S. Cl. ............... 607/2; 607/46; 607/48; 600/559; 600/595; 73/585

(58) Field of Classification Search ............... 607/2, 46, 607/48; 600/559, 595; 73/585
See application file for complete search history.

(56) References Cited

U.S. PATENT DOCUMENTS

| 4,246,913 A | 1/1981 | Ogden et al. |
| 5,762,612 A | 6/1998 | Campbell |
| 6,063,046 A | 5/2000 | Allum |
| 6,219,578 B1 | 4/2001 | Collins et al. |
| 6,366,813 B1 | 4/2002 | DiLorenzo |
| 7,150,715 B2 | 12/2006 | Collura et al. |
| 2002/0026219 A1 | 2/2002 | Collins et al. |
| 2003/0068605 A1 | 4/2003 | Kullok et al. |
| 2003/0100367 A1 | 5/2003 | Cooke |
| 2004/0049124 A1* | 3/2004 | Kullok et al. ............... 600/558 |
| 2005/0119703 A1 | 6/2005 | DiLorenzo |
| 2005/0240253 A1* | 10/2005 | Tyler et al. ............... 607/134 |
| 2006/0058701 A1* | 3/2006 | Bolles et al. ............... 600/558 |
| 2006/0241718 A1 | 10/2006 | Tyler et al. |
| 2007/0197274 A1 | 8/2007 | Dugan |
| 2007/0208403 A1 | 9/2007 | Della Santina et al. |
| 2007/0250119 A1 | 10/2007 | Tyler et al. |

(Continued)

OTHER PUBLICATIONS

Day, Brian L.; "Galvanic Vestibular Stimulation: New Uses for an Old Tool"; The Journal of Physiology; dated 1999; pp. 631; vol. 517; located at: http://jp.physoc.org/cgi/content/full/517/3/631.

(Continued)

Primary Examiner — Nicole F Lavert

(57) ABSTRACT

A system is generally described for altering a user's motional response to sensory input and includes a current source and a first sensory input device configured to provide a first sensory input to a user. The system also includes a second sensory input device configured to provide a second sensory input to a user and a sensor device configured to detect motions associated with the user. Further, the system includes a control unit configured to receive signals from the sensor and receive sensory signals related to the first and second sensory inputs. The control unit generates control signals based on the signals and the sensory signals. Further still, the system includes electrical contacts configured to contact flesh of the user and deliver current from the current source to the vestibular system of the user in response to the control signals and the current is configured to cause the user to move in a predetermined manner if the user is not in the process of making the predetermined motion.

35 Claims, 12 Drawing Sheets

U.S. PATENT DOCUMENTS

| | | |
|---|---|---|
| 2008/0243005 A1 | 10/2008 | Jung et al. |
| 2009/0046140 A1 | 2/2009 | Lashmet et al. |
| 2009/0117525 A1 | 5/2009 | Bavaro et al. |

OTHER PUBLICATIONS

Fitzpatrick, Richard et al.; "Effects of Vestibular Stimulation Galvanic During Human Walking"; Journal of Physiology; dated 1999; pp. 931-939; vol. 517.3; located at: http://jp.physoc.org/cgi/content/abstract/517/3/931.

Fitzpatrick, Richard et al.; "Task-Dependent Reflex Responses and Movement Illusions Evoked by Galvanic Vestibular Stimulation in Standing Humans"; Journal of Physiology; dated 1994; pp. 363-372; vol. 478.2; located at: http://jp.physoc.org/cgi/content/abstract/478/Pt_2/363.

Maeda, Taro et al.; "Shaking the World: Galvanic Vestibular Stimulation as a Novel Sensation Interface"; NTT CS Lab; pp. 1 of 1; located at: http://www.hi.mce.uec.ac.jp/inami-lab/local/siggraph2005/Shaking_the_world.pdf.

Maeda, Taro et al.; "Virtual Acceleration with Galvanic Vestibular Stimulation in a Virtual Reality Environment"; Proceedings of the IEEE Virtual Reality; dated Mar. 12-16, 2005; pp. 289-290; vol. VR '05.

Nagay, Naohisa et al.; "Visual Perception Modulated by Galvanic Vestibular Stimulation"; ACM International Conference Proceeding Series; dated 2005; pp. 78-84; vol. 157; located at: http://portal.acm.org/citation.cfm?id=1152399.1152415.

"Parasitic Humanoid"; pp. 1-10; printed on Oct. 2, 2008; located at: http://www.brl.ntt.co.jp/people/parasite/.

"Transcutaneous Electrical Nerve Stimulator"; Wikipedia, the Free Encyclopedia; pp. 1-2; located at: http://en.wikipedia.org/wiki/Transcutaneous_Electrical_Nerve_Stimulator.

\* cited by examiner

SYSTEM FOR ALTERING MOTIONAL RESPONSE TO SENSORY INPUT

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

For purposes of the USPTO extra-statutory requirements, the present application constitutes a continuation-in-part of U.S. patent application Ser. No. 12/290,635, entitled SYSTEM FOR ALTERING MOTIONAL RESPONSE TO MUSIC, naming Alistair K. Chan, Roderick A. Hyde, Jordin T. Kare and Lowell L. Wood, Jr. as inventors, filed 31, OCTOBER, 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,636, entitled SYSTEM AND METHOD OF PROVIDING FEEDBACK CONTROL IN A VESTIBULAR STIMULATION SYSTEM, naming Alistair K. Chan, Roderick A. Hyde, Jordin T. Kare and Lowell L. Wood, Jr. as inventors, filed 31, OCTOBER, 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,680, entitled ADAPTIVE SYSTEM AND METHOD FOR ALTERING MOTION OF A PERSON, naming Alistair K. Chan, Roderick A. Hyde, Jordin T. Kare and Lowell L. Wood, Jr. as inventors, filed 31, OCTOBER, 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,666, entitled SYSTEM AND METHOD FOR PROVIDING THERAPY BY ALTERING THE MOTION OF A PERSON, naming Alistair K. Chan, Roderick A. Hyde, Jordin T. Kare and Lowell L. Wood, Jr. as inventors, filed 31, OCTOBER, 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,667, entitled SYSTEM AND METHOD FOR GAME PLAYING USING VESTIBULAR STIMULATION, naming Alistair K. Chan, Roderick A. Hyde, Jordin T. Kare and Lowell L. Wood, Jr. as inventors, filed 31, OCTOBER, 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,668, entitled SYSTEM AND METHOD OF TRAINING BY PROVIDING MOTIONAL FEEDBACK, naming Alistair K. Chan, Roderick A. Hyde, Jordin T. Kare and Lowell L. Wood, Jr. as inventors, filed 31, OCTOBER, 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,630, entitled SYSTEM AND METHOD OF ALTERING MOTIONS OF A USER TO MEET AN OBJECTIVE, naming Alistair K. Chan, Roderick A. Hyde, Jordin T. Kare and Lowell L. Wood, Jr. as inventors, filed 31, OCTOBER, 2008, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

BACKGROUND

The description herein generally relates to the field of alteration of a user's motional response to music or other sounds. The description also relates to the field for altering a user's motions in response to stimuli or in response to training signals.

Conventionally, there is a need for systems and methods to induce human's or animal's movements. Such induced movement may be accomplished through the electrical stimulation of the vestibular system of humans or animals. Conventionally, vestibular stimulation is not done in a controlled manner using feedback control mechanisms and further has not been conceived to be applied in various ways, when combined with such feedback control mechanisms.

Accordingly, there is a need for systems and methods to stimulate the vestibular systems of humans or animals in a controlled manner to provide desirable results. Such feedback systems may be applied in a variety of settings to provide training, therapy, and entertainment, among other applications.

SUMMARY

In some aspects, methods may be provided for altering a user's motional response to sensory inputs.

In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer. Also various structural elements may be employed depending on design choices of the system designer.

In some aspects, systems may be provided for altering a user's motional response to sensory input includes a current source and a first sensory input device configured to provide a first sensory input to a user. The system also includes a second sensory input device configured to provide a second sensory input to a user and a sensor device configured to detect motions associated with the user. Further, the system includes a control unit configured to receive signals from the sensor and receive sensory signals related to the first and second sensory inputs. The control unit generates control signals based on the signals and the sensory signals. Further still, the system includes electrical contacts configured to contact flesh of the user and deliver current from the current source to the vestibular system of the user in response to the control signals and the current is configured to cause the user to move in a predetermined manner if the user is not in the process of making the predetermined motion.

In another aspect, a system for altering a user's motional response to sensory input includes a current source, a first sensory input device configured to provide a first sensory input to a user, and a second sensory input device configured to provide a second sensory input to a user. Further, the system includes a sensor device configured to detect motions associated with the user. Further still, the system includes a control unit configured to receive signals from the sensor and receive sensory signals related to the first and second sensory inputs. The control unit generates control signals based on the signals and the sensory signals. Further still, the system includes electrical contacts configured to contact flesh of the user and deliver current from the current source to the vestibular system of the user in response to the control signals and the current is configured to cause the user to move in a predetermined manner after the user fails to make the predetermined motions.

In yet another aspect, a system for altering a user's motional response to sensory input from more than one sensory input device includes a current source, a first sensory input device configured to provide a combined first and second sensory input to a user, and a second sensory input device configured to provide a third sensory input to a user. The system also includes a sensor device configured to detect motions associated with the user. Further, the system includes a control unit configured to receive signals from the sensor and receive sensory signals related to the first and second sensory inputs. The control unit generates control signals based on the signals and the sensory signals. Further still, the system includes electrical contacts configured to contact flesh of the user and deliver current from the current source to the vestibular system of the user in response to the control signals and the current configured to cause the user to move in a predetermined manner after the user fails to make the predetermined motions.

In still yet another aspect, a system for altering a user's motional response to sensory input from more than one sensory input device includes a current source, a first sensory input device configured to provide a combined first and second sensory input to a user, and a second sensory input device configured to provide a third sensory input to a user. A sensor device is configured to detect motions associated with the user. The system also includes a control unit configured to receive signals from the sensor and receive sensory signals related to the first and second sensory inputs. The control unit generates control signals based on the signals and the sensory signals. Further, the system includes electrical contacts configured to contact flesh of the user and deliver current from the current source to the vestibular system of the user in response to the control signals and the current configured to cause the user to move in a predetermined manner if the user is not in the process of making the predetermined motion.

In yet still another aspect, a system for altering a user's motional response to motional input includes a current source and a motion inducement platform, inducing motion of at least a portion of the user. The system also includes a first sensor device configured to detect motions associated with the user. The system also includes a control unit configured to receive signals from the first sensor and generating control signals based on the signals from the first sensor. Further, the system includes electrical contacts configured to contact flesh of the user and deliver current from the current source to the vestibular system of the user in response to the control signals and the current configured to induce the user to move in a manner responsive to the induced motion of at least a portion of the user.

In addition to the foregoing, other system aspects are described in the claims, drawings, and text forming a part of the present disclosure.

In addition to the foregoing, various other method and/or system and/or program product aspects are set forth and described in the teachings such as text (e.g., claims and/or detailed description) and/or drawings of the present disclosure.

The foregoing is a summary and thus contains, by necessity, simplifications, generalizations and omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

The foregoing summary is illustrative only and is not intended to be in any way limiting. In addition to the illustrative aspects, embodiments, and features described above, further aspects, embodiments, and features will become apparent by reference to the drawings and the following detailed description, of which.

DETAILED DESCRIPTION

Figure 1:
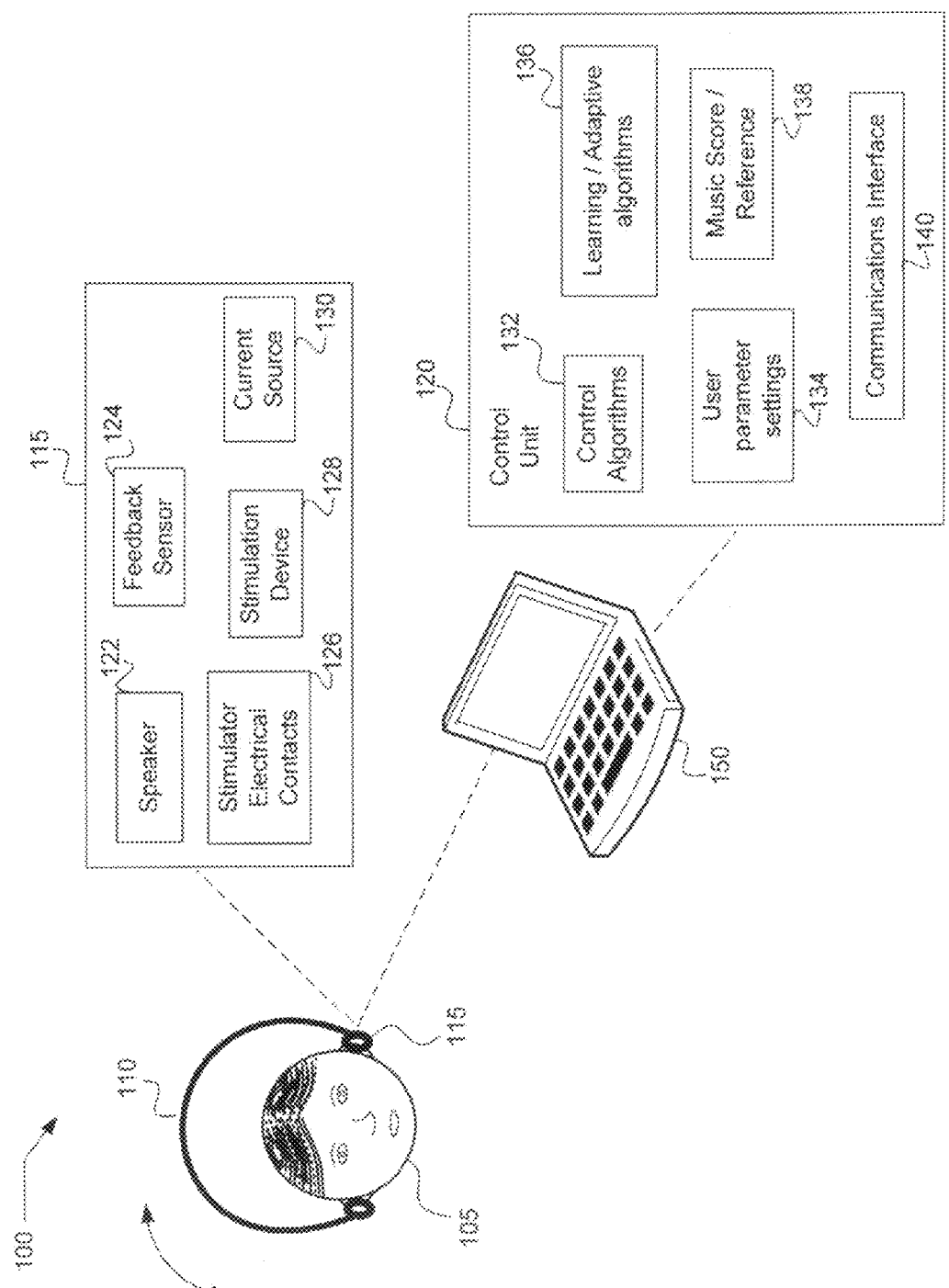
FIG. 1 is an exemplary diagram of a vestibular stimulation system in accordance with an exemplary embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.). Further, those skilled in the art will recognize that the mechanical structures disclosed are exemplary structures and many other forms and materials may be employed in constructing such structures.

Galvanic vestibular stimulation is a method in which a stimulus current is provided to the vestibular system of the human body. This is accomplished by providing electrical contacts or otherwise providing electrical stimulation of the nerves near the vestibular site. For example, the contacts may be provided near the mastoid processes on the human head. Galvanic stimulation of the vestibular organs may be achieved by passing a small current between the mastoid processes. In some studies, it has been shown that a large galvanic body sway can be evoked by galvanic vestibular stimulation. Further, it has been shown that rocking or bobbing of the head may also be accomplished.

Further, by providing stimulation at different frequencies, patterns, and magnitudes, other movements may be achieved. In general, the vestibular system detects head movement by sensing head acceleration with specialized peripheral receptors in the inner ear that comprise semicircular canals and otolith organs. The vestibular system is important in virtually every aspect of daily life, because head acceleration information is essential for adequate behavior in three-dimensional space not only through vestibular reflexes that act constantly on somatic muscles and autonomic organs, but also through various cognitive functions such as perception of self movement. In galvanic vestibular stimulation, small-amplitude galvanic current is delivered transcutaneously or via other methods to the vestibular afferents that lie directly below the mastoid bones.

Galvanic vestibular stimulation has many uses. For example, galvanic vestibular stimulation may be used for game playing, therapy, movement training, music enjoyment, and other varied uses. Galvanic vestibular stimulation may be accomplished through, methods and structures. Such methods and structures may include different control algorithms, sensors, inputs, programs, etc. and may be applied in order to enable galvanic vestibular stimulation in an application setting. Referring now to FIG. 1, a generalized schematic of a vestibular stimulation system for a user is depicted. System 100 includes a headset 110 having earphones or earbuds 115 and a control unit 120 attached thereto. Earbuds 110 include a speaker 122, a feedback sensor 124, stimulator contacts 126, a stimulation device 128 and a current source 130. Any or all of these structures may be included in headset 110 or may be elsewhere such as in control unit 120 or associated with a computer 150 or other processing device. Control unit 120 may include control algorithms 132, user parameter settings 134, learning or adaptive algorithms 136, and a database including music and/or a score or other reference information 138. Control unit 120 may also include a communications interface 140. Communications interface 140 may be used to communicate with any of a variety of devices including but not limited to a processing device, such as a computer 150.

In use, headset 110 may be worn by a user 105. Headset 110 may include vestibular stimulator contacts 126 which may be surface electrodes, which may or may not use a contact conductive gel or other chemical placed between the skin and the electrodes. In an exemplary embodiment, it may be possible to induce or influence user motion by using any of a variety of protocols resulting in different performance. For example it may be possible to stimulate the user by using a sine wave current with a frequency in the range of 1 to 2 Hz. The amplitude of such stimulation may be in the range of a few tenths of a milliamp to a few milliamps. The stimulation may occur over a period of just a few seconds to several seconds. All of these factors depend on the performance to be achieved. Such performance may be discovered through training, modeling or through experimentation.

In accordance with an exemplary embodiment, galvanic vestibular stimulation system 100 or like systems may be used to stimulate the vestibular system of a user and cause various motional effects including, but not limited to rocking or swaying of the head, rocking or swaying of the body, induce walking or change of direction of walking, among others.

Figure 2:
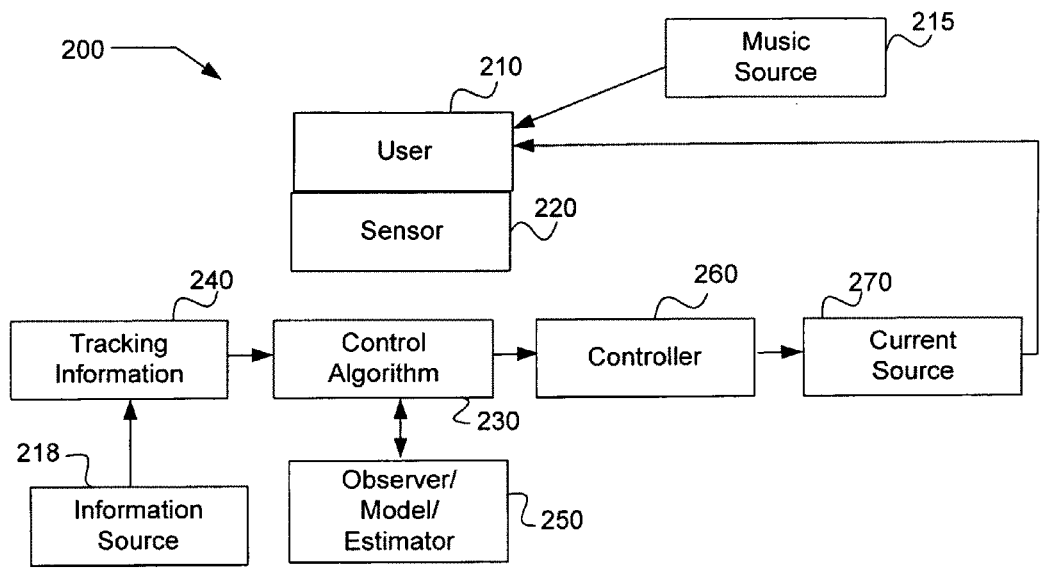
FIG. 2 is an exemplary block diagram of a vestibular stimulation system in accordance with an exemplary embodiment.

Referring now to FIG. 2, a system 200 for altering a user's motional response to music or to other sounds is depicted. System 200 includes, but is not limited to a user 210, having a sensor 220 associated therewith. Sensor 220 may be any of a variety of sensors including accelerometers, strain gauges gyros, laser gyros, MEMS gyros, current sensors, magnetic field sensors, velocity sensors, angular orientation sensors, etc. In one exemplary embodiment a music source 215 is provided to user 210. Music source 215 may include any of a variety of musical pieces or other sounds, sequences of sounds, or patterns of sounds. Also, in an exemplary embodiment the music being played by music source 215 may correspond to certain characteristics which are reflected in an information source 218 that contains various characteristics of the music being played by music source 215. Sensor 220 may be coupled to a control algorithm 230 that receives tracking information from tracking information 240. Traffic tracking information 240 is related to the characteristics of the musical piece or sounds that are stored in information source 218. In one exemplary embodiment an observer, a model, or an estimator may be used in control algorithm 230 to model the user reaction 210. Controller 260 may also be used to control the processes in order to drive the user's reaction to music source 215 towards a predetermined or pre-generated goal. In accordance with exemplary system 200, controller 260 is coupled to a current source 270. Controller 260 provides control signals to current source 270 in order to vary the current delivered by the vestibular stimulation system, such as vestibular stimulation system 100, in order to alter or induce alteration of the motional response of user 210.

In one exemplary embodiment, music may be delivered through a sound delivering device which may include any of a variety of sound delivering mechanisms such as but not limited to earphones, earbuds, speakers, etc. Further, in another exemplary embodiment control unit 260 may be defined by control algorithms 230 and may include user definable settings, user adjustable settings, adaptive settings, adaptive settings that may be different for various users or may be individualized or customized for individual users, etc. Various characteristics may be adapted from the music or sound source, such as but not limited to beats, rhythms, notes, rests, note types, etc. In one exemplary embodiment it may be desired to have a user react in a certain way to a series of sounds such as music. For example, it may be desired to induce a user to rock or sway to a specific beat. It may be that the user is incapable of keeping a proper beat, or a proper rhythm and therefore is encouraged or induced to do so by the stimulation provided by system 200. Such a system may be used in an effort to improve the user's response to music, to provide a more enjoyable experience or to provide an entertainment experience.

In accordance with one exemplary embodiment control algorithm 230 may include an objective function. Further, control algorithm 230 maybe used to track the information such as the beat information or the rhythm information. Further still, control algorithm 230 may include any of or any combination of an observer 250, a classical control algorithm, a nonlinear control algorithm, an optimal control algorithm, a state estimator, an adaptive control algorithm, a Kalman filter, etc. In one exemplary embodiment, control algorithm 230 may include a model of the user's response to electrical current stimulus to the vestibular system in order to estimate the needed stimulation signals. Further, in an exemplary embodiment, the controller 260 may include user definable settings, user adjustable settings, adaptive settings, adaptive settings that may be different for each user, etc. In another exemplary embodiment, sensor 220 may include any of or any combination of at least one accelerometer, at least one strain gauge, at least one gyro, at least one MEMs gyro, at least one laser gyro, at least one current sensor, magnetic field sensors, etc. In one exemplary embodiment, the user may be encouraged to follow any of a variety of characteristics including following beats, rhythms, notes, rests, note types, or any combination of these or other characteristics of the sounds. Further still, such characteristics may be selectable and the magnitude of the current delivered may be adjustable.

Figure 8:
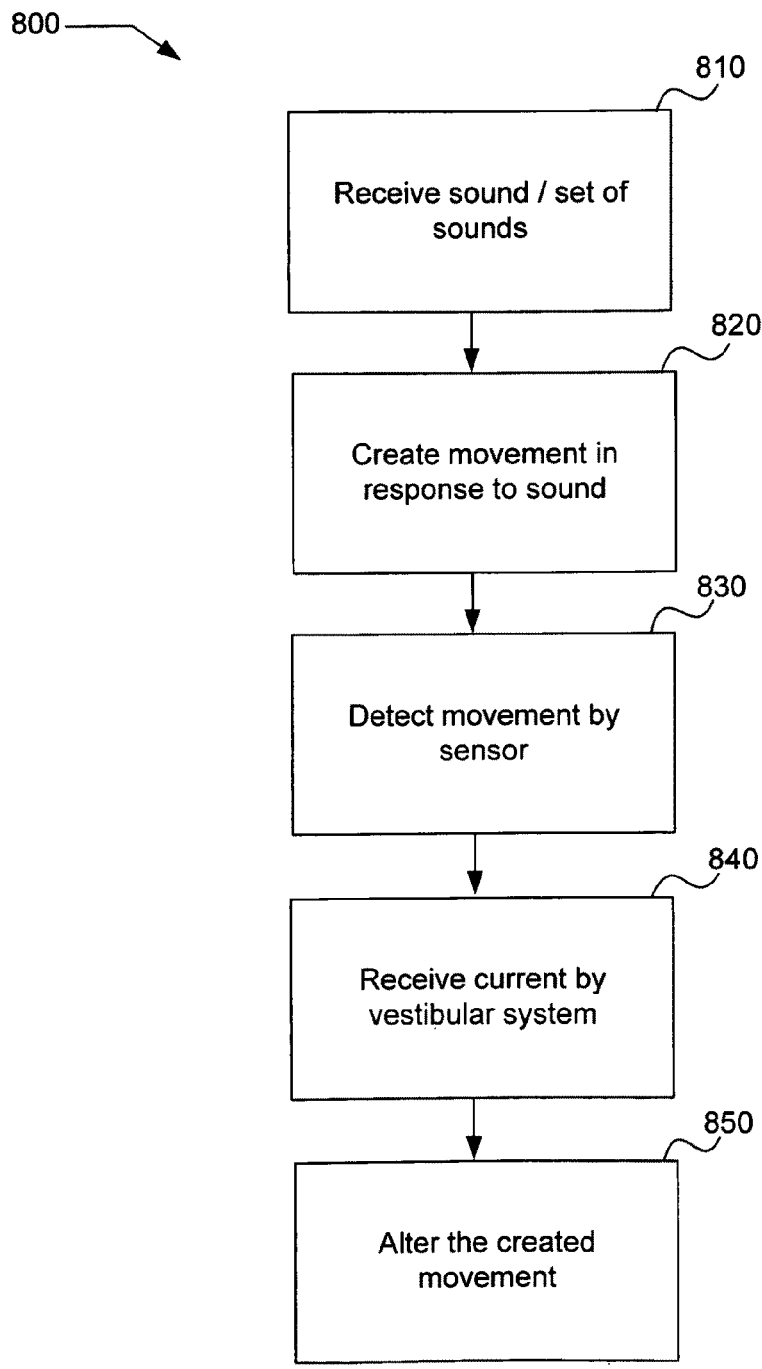
FIG. 8 is an exemplary diagram of process for using a vestibular stimulation system in accordance with an exemplary embodiment.

Referring now to FIG. 8, a process 800 for altering a user's motional response to sound may include receiving a sound produced by a device capable of producing sound (process 810). A sound device may be in communication with a sound data source. The sound data source may include information associated with at least one set of sounds. Movement may be created in response to the received sound (process 820). The movement may be detected by a feedback sensor device and compared to information from an information source including information associated with at least one characteristic of the at least one set of sounds. The comparison information may be provided to a control program. The control program may have a control algorithm configured to generate control data based on the comparison. In one exemplary embodiment movement may be detected by a sensor (process 830). A current may be received by a vestibular system from electrical contacts coupled to a current source (process 840). The current may be delivered based on the control data and output control signals. The created movement may be altered in response to the current (process 850).

In one exemplary embodiment the altered movement may be involuntary in response to the current. In another exemplary embodiment the control algorithm may include an objective function, may be configured to track the information, may include an observer, may include a classical control algorithm, may include a nonlinear control algorithm, may include an optimal control algorithm, may include a State estimator, may include an adaptive control algorithm, may include a Kalman filter, etc. Further, in exemplary embodiment, the control algorithm may include a model of the user's response to electrical current stimulus to the vestibular system in order to calculate the amount of current needed.

Figure 9:
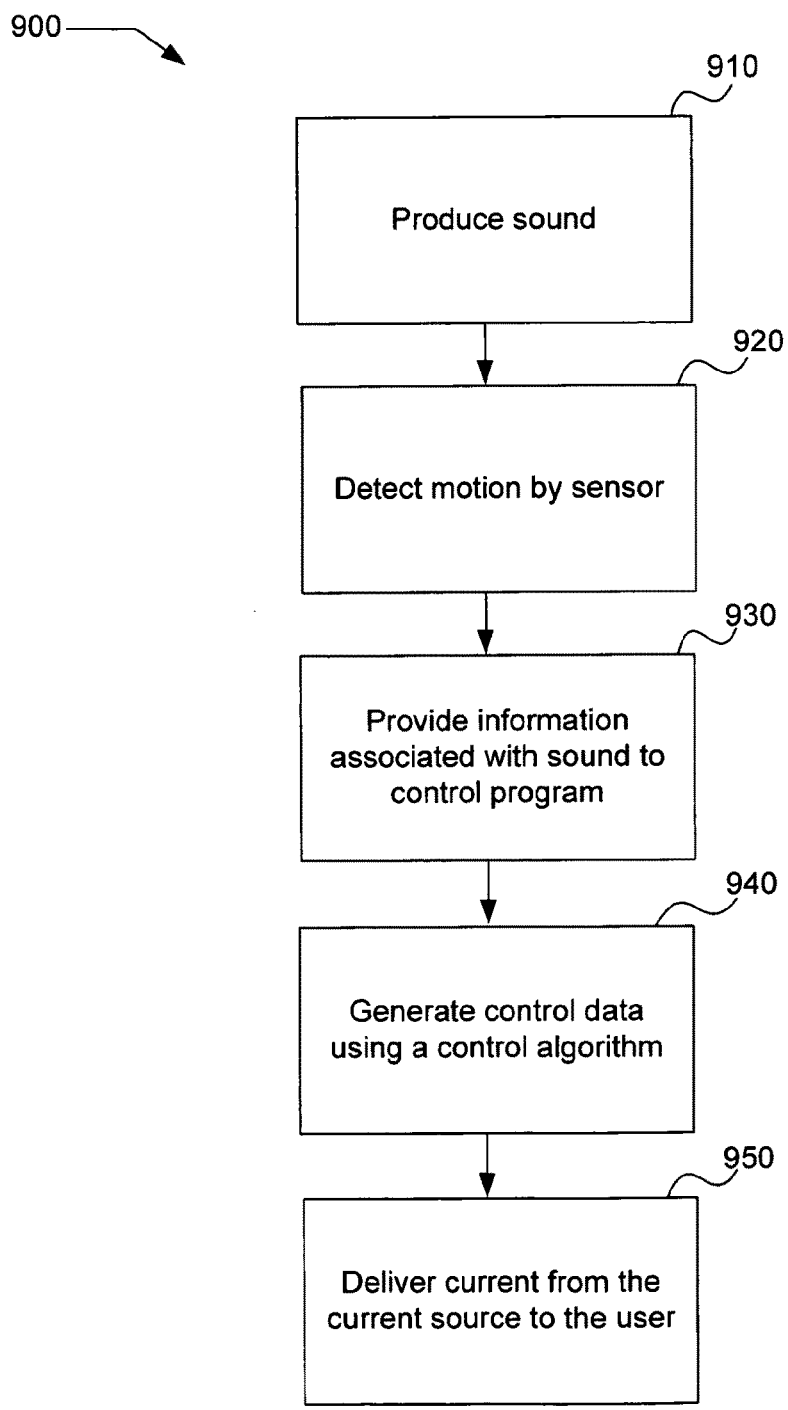
FIG. 9 is an exemplary diagram of another process for using a vestibular stimulation system in accordance with an exemplary embodiment.

In accordance with another exemplary embodiment, a process 900 is depicted in FIG. 9 for altering a users motional response to sound. Process 900 includes producing a sound from a sound device capable of producing sound (process 910). A sound device may be in communication with the sound data source. The sound data source includes information associated with at least one set of sounds. Process 900 also includes detecting motions by a feedback sensor device (process 920). The motions may be associated with the user. Further, process 900 includes providing information from an information source including information associated with at least one characteristic of the at least one set of sounds (process 930). The information may be provided to a control program configured to receive data representative of the detected motions and to receive the information. Further still, process 900 includes generating, by the control program, control data based on the data representative of the detected motions and the information (process 940). The control program is configured to receive data representative of the detected motions and to receive the information. The control program has a control algorithm that is configured to generate control data based on the data that is representative of the detected motions and the information. The control program is run by the controller and is configured to output control signals based on the control data. Current may then be delivered from the current source to electrical contacts (process 950). The electrical contacts may be configured to contact flesh of the user, to deliver current to the vestibular system of the user in response to the control signals.

Figure 3:
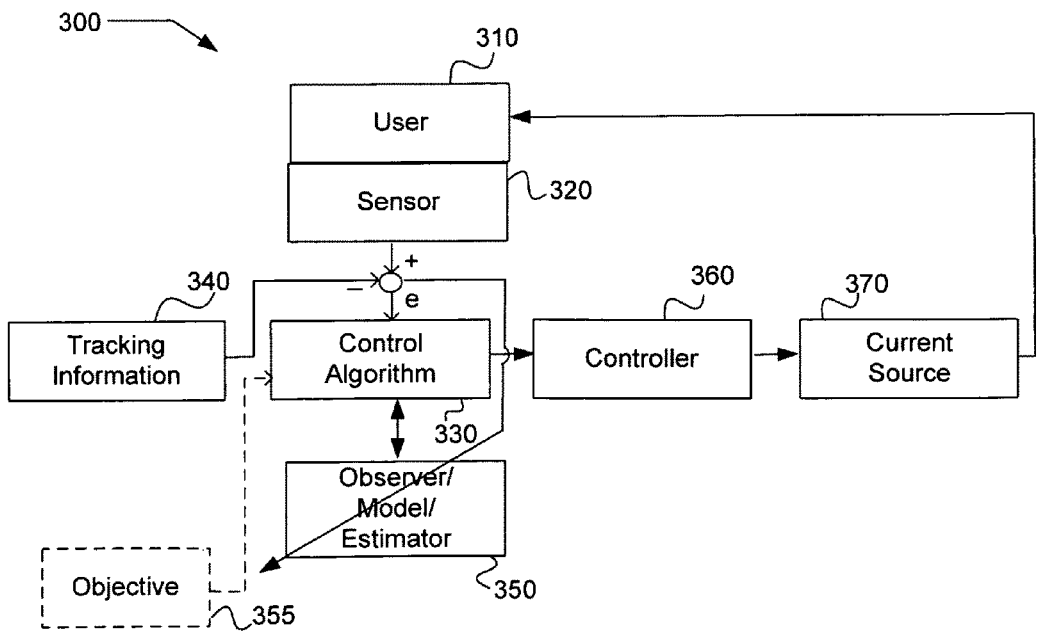
FIG. 3 is an exemplary block diagram of another vestibular stimulation system in accordance with an exemplary embodiment.

Referring now to FIG. 3, a block diagram 300 of an exemplary system for altering a user's motions is depicted. System 300 includes a user 310, and a sensor 320. that is configured to detect motions associated with the user. In one exemplary embodiment, a control algorithm receives information from sensor 320. Such information may be in the form of an error signal reporting error between the user's actual motions and specified tracking information 340. Control algorithm 330 also receives information from an observer, a model, or an estimator 350. In one exemplary embodiment, control algorithm 330 may receive information from an objective 355. Further, in an exemplary embodiment the error may be used to make adjustments to the observer, the model or the estimator 350. The object of the observer, model, or estimator 350 and its adaptability or adjustability is to improve the action of control algorithm 330 run by controller 360 to output currents signals from the current source 370 back to user 310.

Figure 4:
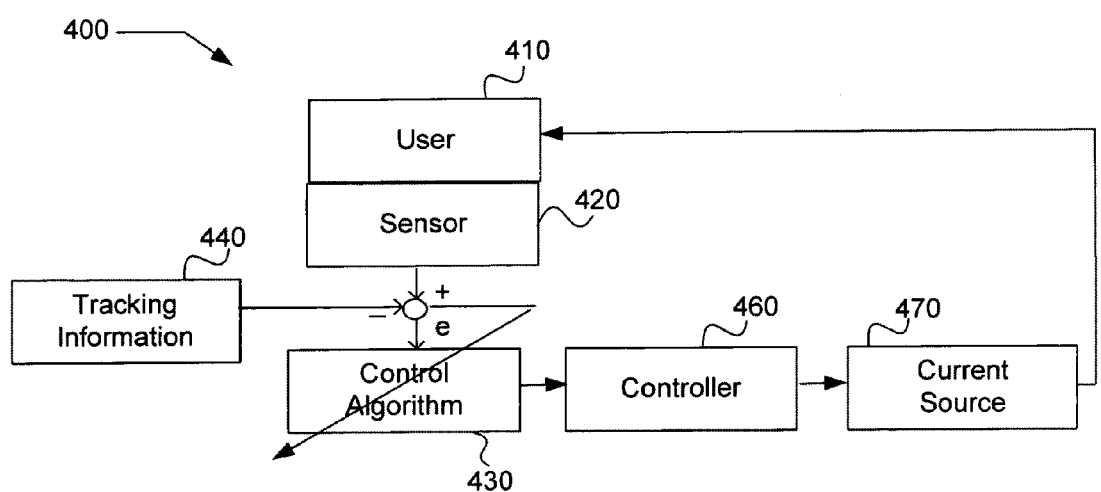
FIG. 4 is an exemplary block diagram of another vestibular stimulation system in accordance with an exemplary embodiment.

Referring now to FIG. 4, a block diagram 400 of an exemplary system for altering a user's motions is depicted. System 400 may include a user 410, and a sensor 420 that is configured to detect motions associated with the user. An objective information source such as tracking information 440, may be configured to receive data representative of the detect motions and to receive the information. The control program may have a control algorithm 430 that is configured to generate control data based on the data representative of the detected motions and the information. A controller 460 may be configured to run the control program and to output control signals based on the control data. Electrical contacts may be configured to contact flesh of the user 410 and deliver current from the current source 470 to the vestibular system of the user 410 in response to the control signals.

In one exemplary embodiment, the objective information may be provided by a computer program based on characteristics of the user. The objectives may be provided by a healthcare provider or other source. Further, in one exemplary embodiment, control algorithm 430 receives error feedback and parameters of the control algorithm or the controller may be altered or adapted. Such an adaptive system having adaptive control algorithm 430 may be an effective way to generate initial control algorithms that may be useful when parameters of such control algorithms are unknown or modeling of the processes may be difficult as well as providing high performance systems.

Referring again to FIG. 4, an adaptive system 400 for altering a user's motional response to sound is depicted. System 400 includes a user 410 and a sensor 420 is configured to detect motions associated with the user. A sound source may provide sounds to a user. An information source which may include information associated with at least one characteristic of the at least one set of sounds may be but is not limited to tracking information source 440. A control program is configured to receive data that is representative of the detected motions and to receive the information. The control program has a control algorithm configured to generate control data based on the data representative of the detected motions and the information. Controller 460 is configured to run the control program and output control signals based on the control data. Control algorithm 430 may be an adaptive system configured to adjust parameters of at least one of the controller, the feedback sensor, the sound source, the information, or the control algorithm. A vestibular stimulation device may be configured to deliver current from the current source to the vestibular system of the user in response to the control signals. In one exemplary embodiment, the adaptive system includes a self-learning system. In other exemplary embodiments, the self-learning system may be an artificial intelligence program, a fuzzy logic program, a neural network program, an adaptive control law, an artificial intelligence program, etc. In such an adaptive system, the parameters which are adapted may include any of a variety of parameters including but not limited to control law parameters, speed parameters, intensity parameters, and user specific parameters, among others. The adaptive system may be an on-line self-learning system such that it may be trained and learning may occur during the use phase. In other exemplary embodiments, the self-learning system learns off-line during a training phase in such a configuration it may use a training set of data to learn.

Figure 5:
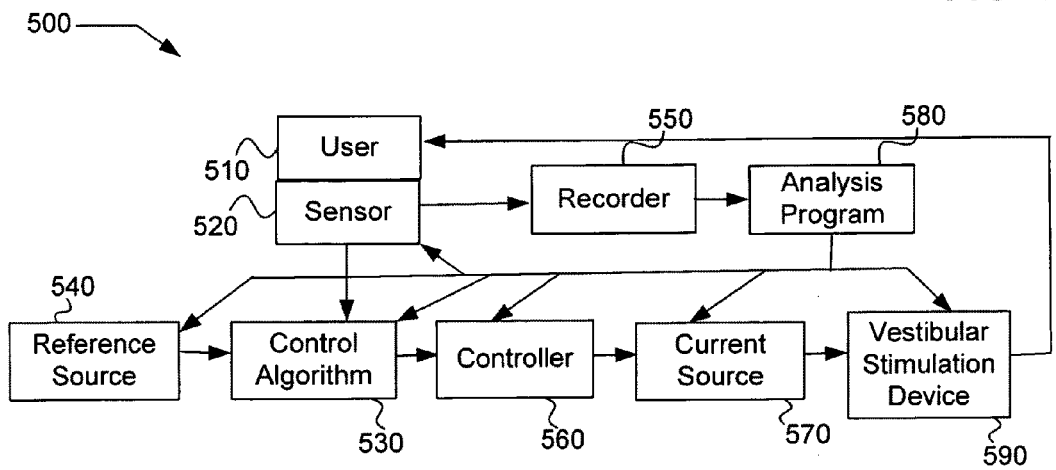
FIG. 5 is an exemplary block diagram of another vestibular stimulation system in accordance with an exemplary embodiment.

Referring now to FIG. 5, a system 500 for altering a user's motional response to sound is depicted. User 510 may have a sensor device 520 configured to detect motions associated with user 510. An objective information source or a reference source 540 is configured to provide information related to an objective of the user's motion. A control program 550 may be configured to receive data representative of the detected motions and receive the information. The control program may be a variety of control algorithms 530 configured to generate control data based on the data representative of the detected motions and the information. A controller 560 may be configured to run the control program and output control signals based on the control data. An adaptive system is configured to adjust parameters of at least one of controller 561, feedback sensor 520, a sound source, reference source 540, control algorithm 530, controller 560, current source 570, or vestibular stimulation device 590. Vestibular stimulation device 590 is configured to deliver current from the current source to the vestibular system of user 510 in response to the control signals.

Figure 10:
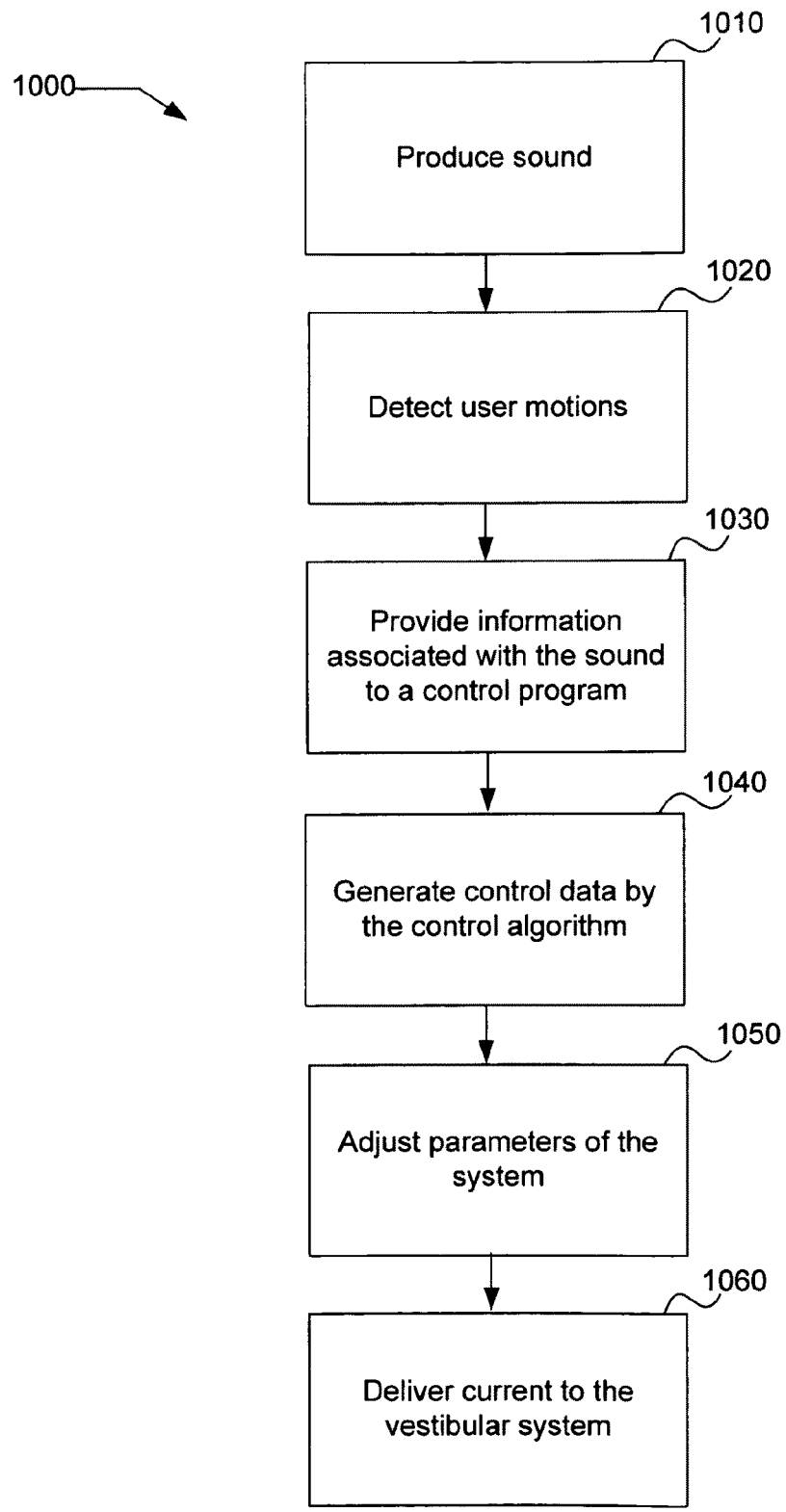
FIG. 10 is an exemplary diagram of another process for using a vestibular stimulation system in accordance with an exemplary embodiment.

Referring now to FIG. 10, a process 1000 for altering a user's motional response to sound, is depicted. Process 1000 includes producing a sound from a sound device capable of producing sound (process 1010). The sound device is in communication with a sound data source. The sound data source includes information associated with at least one set of sounds. Motions are detected from the user by a feedback sensor device. The motions are associated with the user (process 1020). Information is provided from an information source (process 1030). The information includes information that is associated with at least one characteristic of the at least one set of sounds. The information is provided to a control program that is configured to receive data representative of the detected motions and to receive the information. Control data is generated by the control program (process 1040). Control data is based on the data representative of the detect motions and the information. The control program is configured to receive data representative of the detect motions and to receive the information. The control program has a control algorithm that is configured to generate control data based on the data representative of the detected motions and the information. Parameters of the system are adjusted (process 1050). Parameters of the at least one controller, the feedback sensor, the sound source, the information, or the control algorithm may be adjusted by the adaptive system. Current is delivered from the current source to the vestibular system of the user in response to the control signals by a vestibular stimulation device (process 1060).

Referring again to FIG. 5, system 500 may be a system which is used to provide therapy for a user. Such therapy may be for any of a variety of conditions of the user such as, but not limited to users having various diseases, users who have lost function of certain muscles, users who need rehabilitation for walking and other motor control issues. System 500 includes the use of a current source 570, a reference source that includes information associated with desired motions of the user. Such desired motion's may be formulated through experiment or may be provided from a care provider such as a doctor, a therapist, or the like. A recording device 550 may be used to maintain a record of motions of the user. Such a recording device 550 may be used by a doctor, a therapist, or an analysis program 580 who may use the recorded information to determine if further therapy is needed or similarly if a change in therapy is needed. A feedback sensor device 520 is configured to detect motions associated with the user during therapeutic use. Feedback sensor 520 provides sensor information to recording device 550. A control program is configured to receive data representative of the detected motions and to receive the information from the reference source. The control program has a control algorithm 530 that is configured to generate control data based on the data representative of the detected motions and the information. For example, sensor 520 may detect motions of the user and communicate those motions to control algorithm 530 likewise, reference source 540 may communicate desired motions to a control algorithm 530. Control algorithm 530 determines whether the user is making the desired motions or not and then sends control signals via controller 560. Controller 560 is configured to run the control program and output control signals which are based on the control data to a current source and a vestibular stimulation device 590. Vestibular stimulation device 590 provides stimulation to the user to alter or induce the user's motions. Once the user's motions are altered, the user's body may be trained to perform such motions. Such training may be done in a repetitious manner whereby the motions are induced over and over after the user is prompted to perform the motions. An analysis program 580 is configured to analyze information from the recording device and is related to a user's therapeutic progress and to provide changes to at least one of the reference source, the control algorithm, the controller, the current source, or the vestibular stimulation device, depending on the user's progress in therapy.

In accordance with an exemplary embodiment, the analysis program 580 may include an objective function, a target, a performance score, or the like. Such metrics may be used to determine whether the user is improving given the therapy. In another exemplary embodiment, analysis program 580 includes instructions for the user. Such instructions may be instructions to repeat a previous action, or to modify a previous action. Further, in an exemplary embodiment, the analysis program includes functionality to make changes to the information from the reference source, parameters of the control algorithm, parameters of the controller, changes in current magnitude, current frequency, or changes to the vestibular stimulation device.

Figure 6:
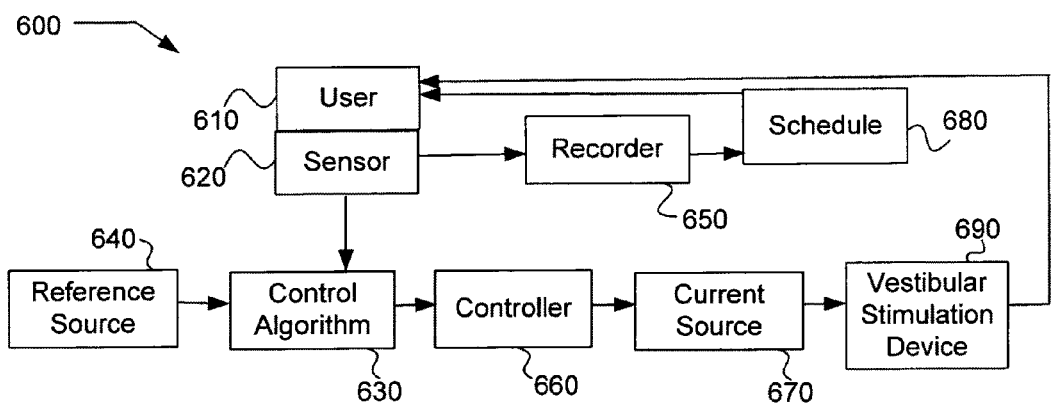
FIG. 6 is an exemplary block diagram of another vestibular stimulation system in accordance with an exemplary embodiment.

Referring now to FIG. 6, a system 600 for providing therapy for a user 610 by altering a user's motional response is depicted. System 600 includes a user 610 having a sensor 620 associated therewith to detect motions of user 610. A recording device 650 may be coupled to sensor 620. Sensor 620 may also deliver information to control algorithm 630. Control algorithm 630 may also receive reference information for reference source 640. Control algorithm 630 is configured to generate control data based on the information from reference source 640 and the sensor information. Controller 660 may be configured to run the control program and output control signals based on the control data generated. The vestibular stimulation device 690 is configured to deliver current from the current source 670 to the vestibular system of the user in response to the control signals. In an exemplary embodiment, a schedule 680 is configured to provide scheduling information to user 610 to attempt to provide therapy for a user condition. Such scheduling information may include information that is scheduled during a period of time in a periodic manner. Further, scheduling information may include a schedule which is not periodic. Further still, such scheduling information may include scheduling therapy at different times of day, at different days of the week, or at different times of the year, etc. The scheduling information may be dictated automatically or may be derived from physicians instructions or the like.

Figure 7:
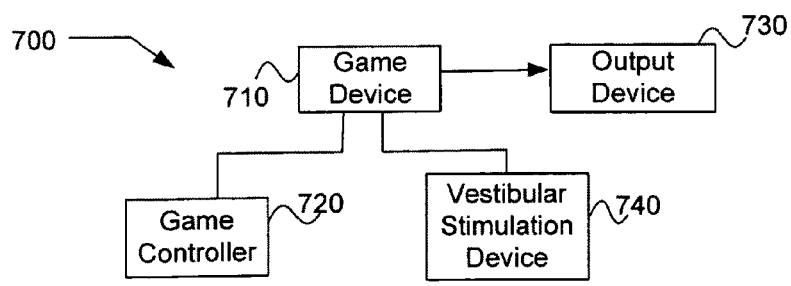
FIG. 7 is an exemplary block diagram of another vestibular stimulation system in accordance with an exemplary embodiment.

Referring now to FIG. 7, a system 700 for gaming is depicted. System 700 includes a game device such as a video game system, a computer, or the like. Gaming device 710 includes any of a variety of output devices 730 in communication with the game device. Such devices include, but are not limited to video devices, audio devices, tactile devices, etc. Game device 720 may receive input from an input device such as a game controller 720 or other types of input devices. In accordance with an exemplary embodiment, game device 710 may be coupled to a vestibular stimulation device 740 that is configured to provide vestibular stimulation to a player or other user. In one exemplary embodiment, a feedback sensor device is configured to detect motions associated with the user and the feedback sensor device may provide information. A game program runs on game device 710. The game program may provide output to the output device, such as video output, and may receive input from the input device or the team controller 720. Motion information may be detected by a sensor. Control signals provided to the vestibular stimulation device are provided to include motions of a user or a game player in response to at least one of the output or the input. In one exemplary embodiment, the feedback sensor may be coupled to be a part of the body of the user. In another exemplary embodiment, the game program, running on the game device 710, may be configured to provide output to the game device and may selectively provide control signals to the vestibular stimulation device to influence motions of the user during first days and then provide the output and receive input from the sensor device during a second phase. This enables games in which the user or the player is provided a certain stimulus and in response to that stimulus should attempt to repeat a set of motions to prevent be during the first phase.

Figure 11:
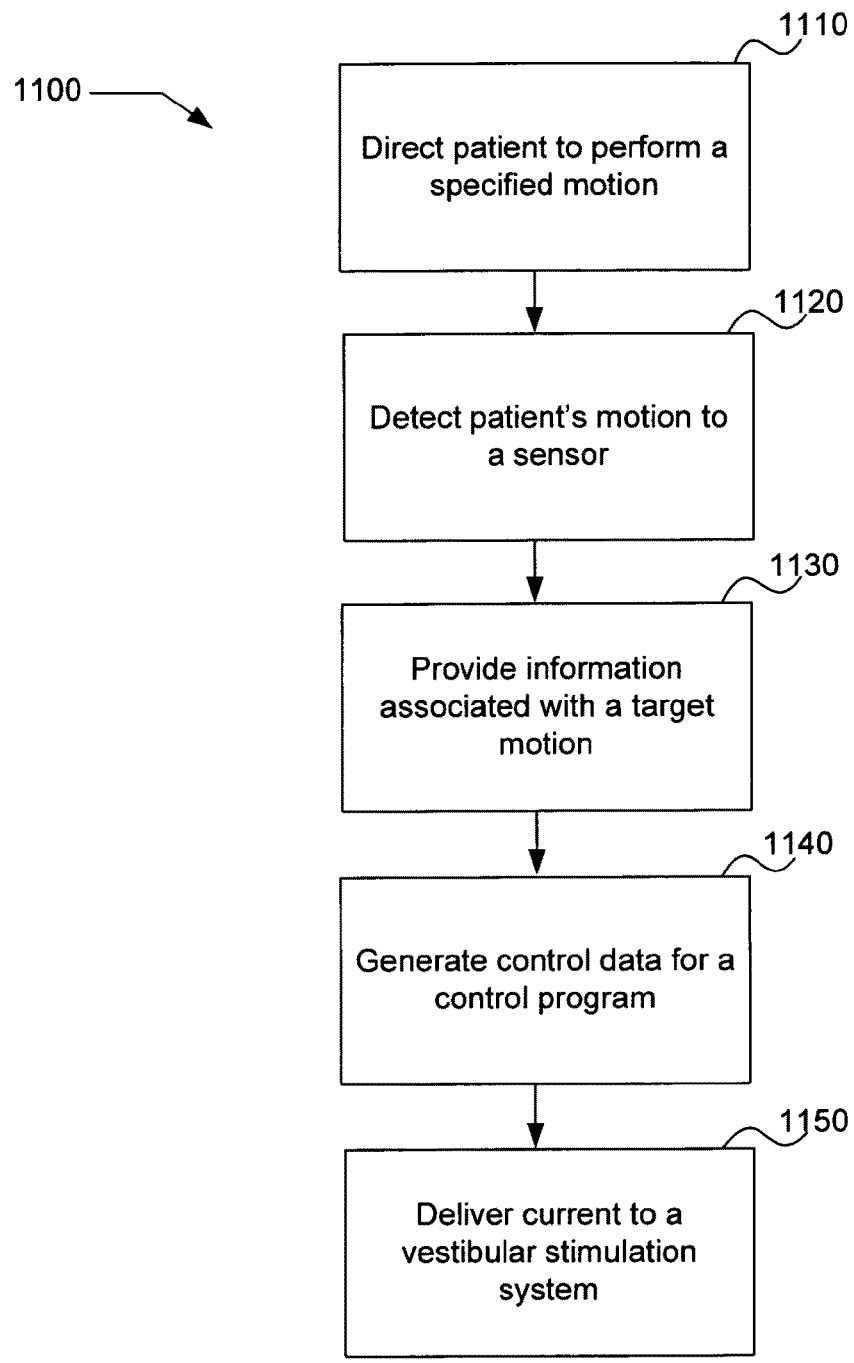
FIG. 11 is an exemplary diagram of another process for using a vestibular stimulation system in accordance with an exemplary embodiment.

Referring now to FIG. 11, a process 1100 for providing motor control therapy for a user by altering the user's motional response, is depicted. Process 1100 includes directing a user to perform a specified motion in accordance with a schedule (process 1110). Process 1100 also includes detecting the user's motions in response to the directions, by a feedback sensor device (process 1120). Further, process 1100 includes providing information associated with a target motion (process 1130). A control program generates control data based on the data that is representative of the motions expected by the sensor and the reference information. The control program is configured to receive data that is representative of the detected motions and to receive the information. The control program has a control algorithm that is configured to generate control data based on the data representative of the detected motions and the information (process 1140). The control program is run by the controller and is configured to output control signals based on the control data. Current is delivered from the current source to the vestibular stimulation device (process 1150). The vestibular stimulation device is configured to deliver a stimulation current to the least one electrical contacts in response to the control signals. The at least one electrical contacts are configured to contact flesh of the user.

Figure 12:
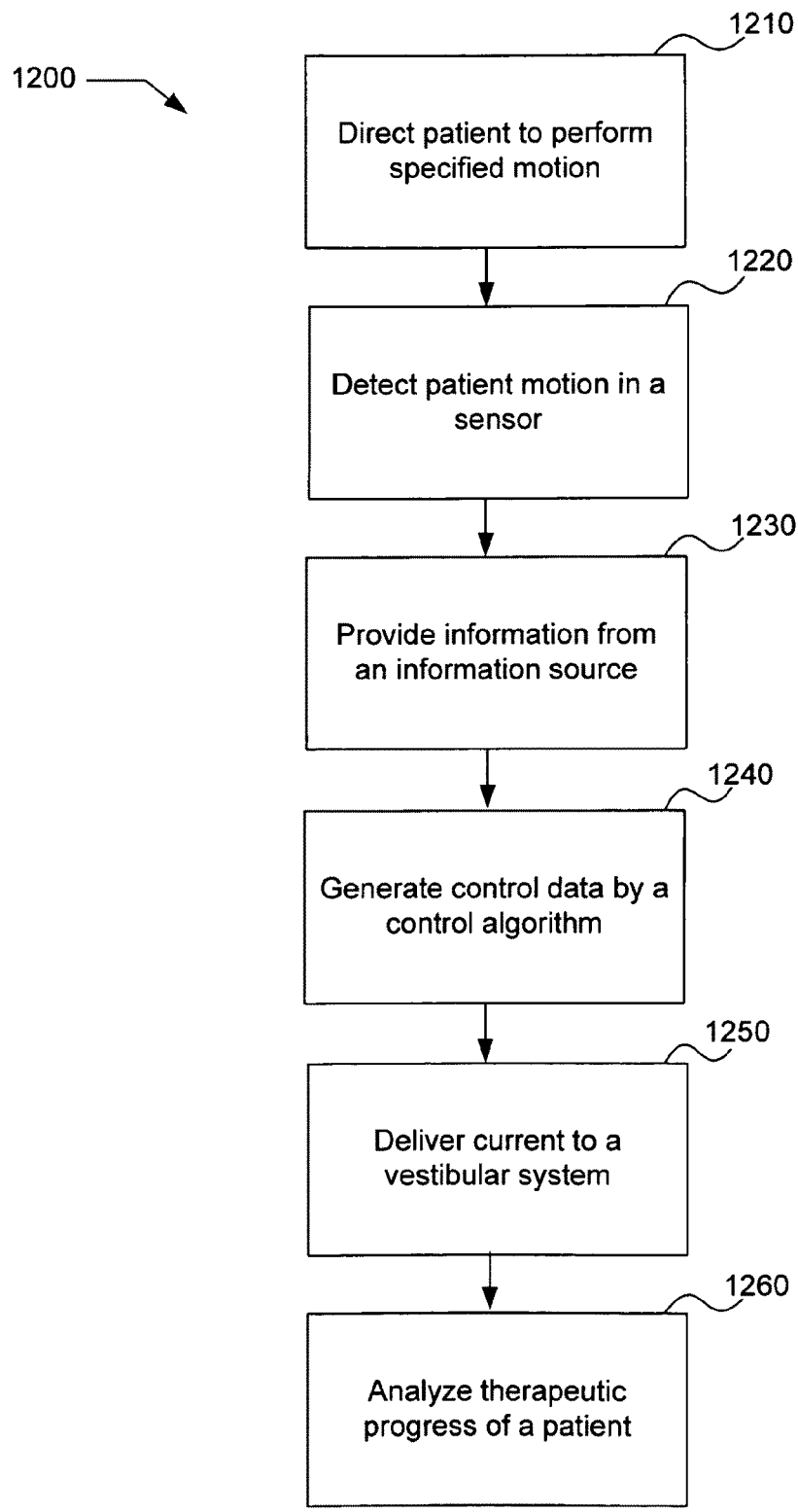
FIG. 12 is an exemplary diagram of another process for using a vestibular stimulation system in accordance with an exemplary embodiment.

Referring now to FIG. 12, a process 1200 for providing motor control therapy for a user by altering a user's motional response, is depicted. Process 1200 includes directing patients to perform specified motions (process 1210). A patient's motions may be detected by a sensor device (process 1220). Information from an information source is provided to a control output (process 1230). Control data is generated by control program (process 1240). Current is delivered to a vestibular stimulation system (process 1250). Analysis is then made of a patient's therapeutic progress (process 1260).

Systems may be provided for training of individual users by altering user's motional responses. Such systems may include many configurations including, but not limited to those in FIGS. 1-6. Such a system may include a current source, and a reference source that has information associated with the sequence of desired motions of a user. The sequence of desired motions may be those on which the user is to be trained. A sensor may be configured to detect motions associated with the user. A control may be configured to receive data representative of the detected motions and also to receive information. The control program has a control algorithm that is configured to generate control data based on the data representative of the subject motions and the information from the reference source. The controller runs the control program and determines control signals based on the control data. The vestibular stimulation device is configured to deliver current from the current source to the vestibular system of the user in response to the control signals, in order to induce a response in the user. The control data effectuate's vestibular stimulation of the user if the user is not in the process of performing the sequence of motions provided by the reference source. In other words, the control data effectuates vestibular stimulation of the user when the user does not perform, either exactly or approximately, motions on which the user is being trained. In accordance with alternative embodiments, the training systems may include evaluation programs which are configured to provide invalidation to a user as to the performance of the user compared with the desired motions. Such evaluation training programs may be valuable in the training process and may be helpful in order to provide the feedback needed by a user to learn the desired motions. Such a system of training may be useful in a variety of situations including, but not limited to learning a set of desired user actions or motions, learning a series of dance steps or motions, learning a set of motions used to operate machinery, learning an athletic movement, or a variety of other situations. In one exemplary embodiment, the vestibular stimulation is provided during the time in which they user is attempting to perform the desired motions. However, in another exemplary embodiment, the user is prompted with vestibular stimulation in a separate training phase. For example, the user may be induced to perform the motion through vestibular stimulation in a first phase and then may try to repeat the motions in a second phase. After the second phase, the performance of the user may be evaluated, scored, etc.

Figure 13:
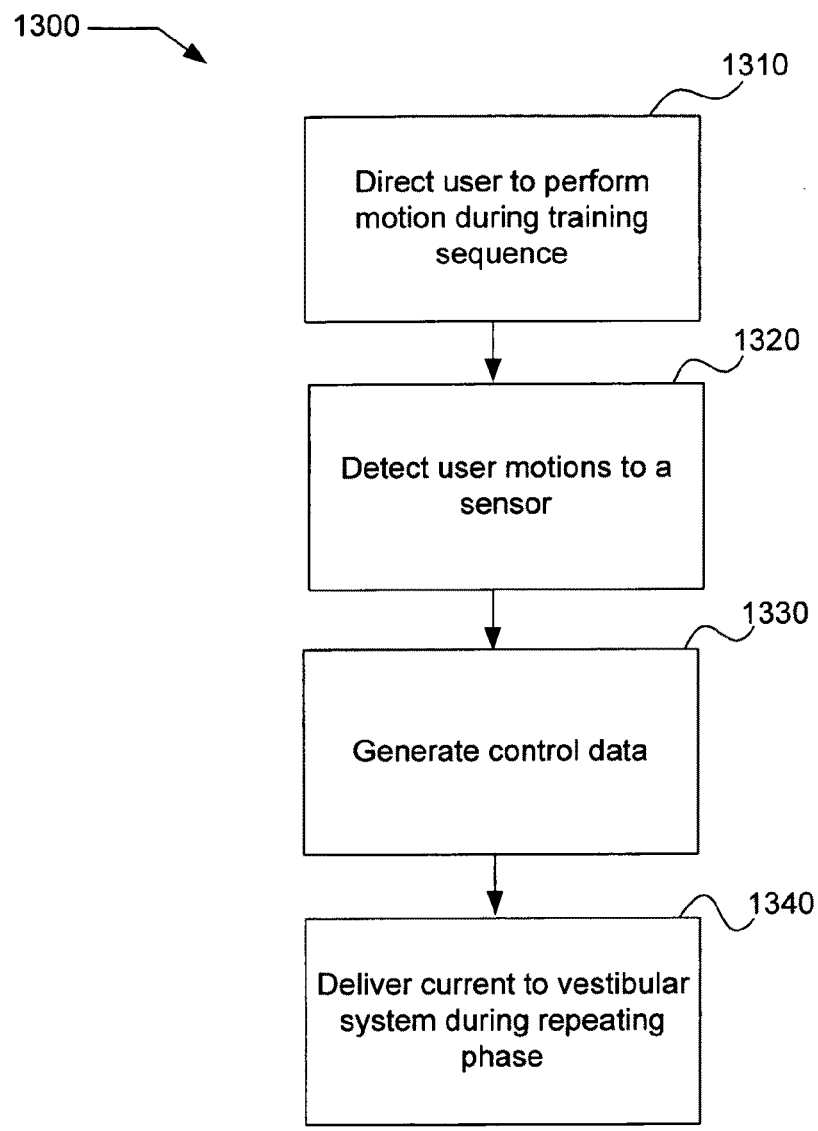
FIG. 13 is an exemplary diagram of another process for using a vestibular stimulation system in accordance with an exemplary embodiment.

Referring now to FIG. 13, a system 1300 is depicted. Process 1300 includes directing a user to perform a specified motion during a training sequence (process 1310). The user's motions are detected by a sensor (process 1320). After the user's motions are detected, control data may be generated based on the detected motions and on the training sequence (process 1330). A control program generates control data which is provided to a controller. Current is then delivered during a repeating phase in which a user attempts to repeat the training sequence (process 1340).

Figure 14:
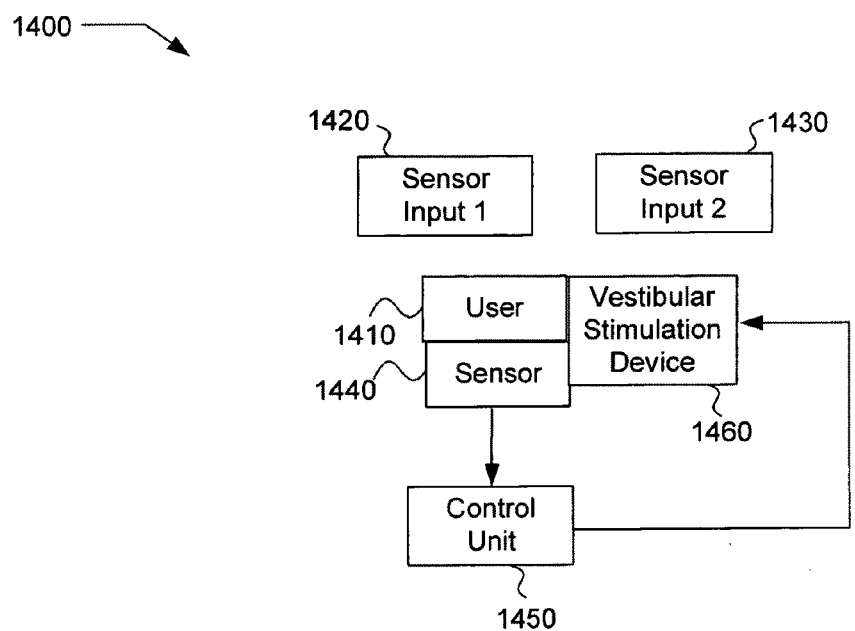
FIG. 14 is an exemplary block diagram of another vestibular stimulation system in accordance with an exemplary embodiment.

Referring now to FIG. 14, a system for altering a user's motional response to sensory input is depicted as system 1400. System 1400 includes a user 1410 receiving sensory input from a first sensory input 1420 and simultaneously receiving a second sensory input from a second sensory input

1430. A sensor device 1440 is configured to detect motions associated with the user. A control unit is configured to receive signals from the sensor and receive sensory signals that are related to the first and second sensory inputs. Control unit 1450 generates control signals based on the signals and the sensory signals. Control unit 1450 outputs information to vestibular stimulation device 1460. The vestibular stimulation device 1460 provides vestibular stimulation to a user's vestibular stimulation system in order to induce movement of the user in a desired manner. In one exemplary embodiment, the current from vestibular stimulation device 1460 may be used to induce the user to move in a predetermined manner if the user is not in the process of making the predetermined motions. In another exemplary embodiment, the current is configured to induce the user to move in a predetermined manner after the user fails to make predetermined motions. For example, if the user performs a series of motions that are imprecise or incorrect, the vestibular stimulation device will provide current to produce or induce the predetermined motions in the user. Further, in another exemplary embodiment, the first sensor input device may be provided to provide a combined first and second sensory input to the user. For example, the device may be a video/audio device in which both video and audio are provided to the user. The second sensory input device may still be provided as a third sensory input to the user, for example may provide a tactile input. Such a tactile input device may be provided on the hand of the user, or any other portion of the body in which the user may feel some input or receive a tactile input.

Figure 15:
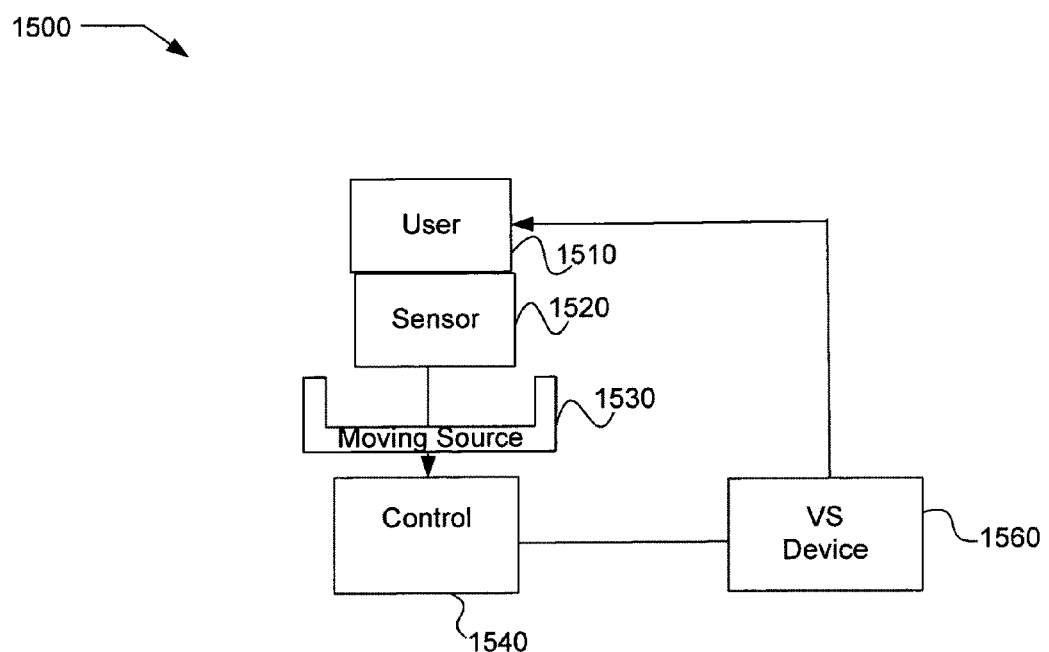
FIG. 15 is an exemplary block diagram of another vestibular stimulation system in accordance with an exemplary embodiment.

Referring now to FIG. 15, a system 1500 is depicted. System 1500 is for altering a user's motional response to motional input. A current source may provide vestibular stimulation through a vestibular stimulation device 1560, as described earlier. In an exemplary embodiment, a motion inducement platform such as a moving source 1530, may induce motion of at least a portion of user 1510. A first sensor device may be configured to detect motions associated with user 1510. A control unit 1540 maybe configured to receive signals from a sensor 1520 and generate control signals based on the signals from sensor 1520. Electrical contacts are configured to contact flesh of user 1510 and deliver current from vestibular stimulation device 1560 in response to the control signals. Current is configured to induce the user to move in a manner that is responsive to the induced motion of at least a portion of the user. In one exemplary embodiment, moving source 1530 may include a vehicle, a road vehicle, an aircraft, a spacecraft, a military vehicle, or the like. Further, in an exemplary embodiment, the goal of vestibular stimulation device 1560 may be too induce cancellation of the induced motion. In another exemplary embodiment, the inducement may be to augment the induced motion by moving source 1530. In another exemplary embodiment, a second sensor may be used that is configured to detect motions of moving source 1530. Such information may be fed directly to control unit 1540. In one or more exemplary embodiments, it may be useful to have such a system in order to provide control of portions of a person's body in a moving environment. For example, it may be desirable to maintain a stable motion of an aircraft pilots head during piloting of an aircraft such as a military aircraft or other performance aircraft. Similarly, such stability of a portion of a person's body may be desired for a spacecraft pilot, a vehicle driver, or the like.

In yet another exemplary embodiment, a system for altering a user's motions may include an objective information source. The objective information source may be configured to provide information related to an objective of the user's motion. For example, the objective may be to perform a certain task. Further, the objective may be to reach a specified goal. In another exemplary embodiment, the objective may be too performed a specified task in a certain amount of time. Further, other objectives may be equally applicable without departing from the scope of the invention. Referring again to FIG. 12, FIG. 12 embodies a process in which an objective may be used. The objective may be provided as information from an information source. Such information source would be an objective information source having at objective user information therein.

In a general sense, those skilled in the art will recognize that the various embodiments described herein can be implemented, individually and/or collectively, by various types of electro-mechanical systems having a wide range of electrical components such as hardware, software, firmware, or virtually any combination thereof and a wide range of components that may impart mechanical force or motion such as rigid bodies, spring or torsional bodies, hydraulics, and electromagnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Quest, Southwestern Bell, etc), or (g) a wired/wireless services entity such as Sprint, Cingular, Nextel, etc.), etc.

One skilled in the art will recognize that the herein described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A system for altering a user's motional response to sensory input, the system comprising:
a current source;
a first sensory input device configured to provide a first sensory input to a user;
a second sensory input device configured to provide a second sensory input to the user;
a sensor device configured to detect motions associated with the user;
a control unit configured to receive signals from the sensor device and receive sensory signals related to the first and second sensory inputs, the control unit generating control signals based on the signals and the sensory signals; and
electrical contacts configured to contact flesh of the user and deliver a current from a current source through the flesh and directly to the vestibular nerve of the user's vestibular system of the user in response to the control signals and the current configured to influence the user to make a predetermined motion if the user is not in a process of making the predetermined motion.

2. The system of claim 1, wherein the first sensory input device includes an audio device.

3. The system of claim 1, wherein the first sensory input device includes a photic device.

4. The system of claim 1, wherein the first sensory input device includes a haptic device.

5. The system of claim 1, wherein the first sensory input device includes a sensory device array.

6. The system of claim 1, wherein the first sensory input device includes an audio device and the second sensory input device includes at least one of a photic device, a haptic device, or an olfactory device.

7. The system of claim 1, wherein the first sensory input device includes a photic device and the second sensory input device includes at least one of an audio device, a haptic device, or an olfactory device.

8. The system of claim 1, wherein the first sensory input device includes a haptic device and the second sensory input device includes at least one of a photic device, an audio device, or an olfactory device.

9. The system of claim 1, wherein the first sensory input device includes an olfactory device and the second sensory input device includes at least one of a photic device, a haptic device, or an audio device.

10. The system of claim 1, wherein the first sensory input device includes a sensor array and the sensor array is distributed over a portion of the user.

11. A system for altering a user's motional response to sensory input, the system comprising:
a current source;
a first sensory input device configured to provide a first sensory input to a user;
a second sensory input device configured to provide a second sensory input to the user;
a sensor device configured to detect motions associated with the user;
a control unit configured to receive signals from the sensor device and receive sensory signals related to the first and second sensory inputs, the control unit generating control signals based on the signals and the sensory signals; and
electrical contacts configured to contact flesh of the user and deliver a current from a current source through the flesh and directly to the vestibular nerve of the user's vestibular system of the user in response to the control signals and the current configured to influence the user to make a predetermined motion after the user fails to make the predetermined motions.

12. The system of claim 11, wherein the first sensory input device includes an audio device.

13. The system of claim 11, wherein the first sensory input device includes a photic device.

14. The system of claim 11, wherein the first sensory input device includes a haptic device.

15. The system of claim 11, wherein the first sensory input device includes an olfactory device.

16. The system of claim 11, wherein the first sensory input device includes a sensory device array.

17. The system of claim 11, wherein the first sensory input device includes a sensor array and the sensor array is distributed over a portion of the user.

18. A system for altering a user's motional response to sensory input from more than one sensory input device, the system comprising:
a current source;
a first sensory input device configured to provide a combined first and second sensory input to a user;
a second sensory input device configured to provide a third sensory input to the user;
a sensor device configured to detect motions associated with the user;
a control unit configured to receive signals from the sensor device and receive sensory signals related to the first and second sensory inputs, the control unit generating control signals based on one or more signals and the sensory signals; and
electrical contacts configured to contact flesh of the user and deliver a current from a current source through the flesh and directly to the vestibular nerve of the user's vestibular system of the user in response to the control signals and the current configured to influence the user to make a predetermined motion after the user fails to make the predetermined motions.

19. The system of claim 18, wherein the first sensory input includes an audio input.

20. The system of claim 18, wherein the first sensory input includes a haptic input.

21. The system of claim 18, wherein the first sensory input includes an olfactory input.

22. The system of claim 18, wherein the first sensory input includes a photic input.

23. The system of claim 18, wherein the third sensory input includes an audio input.

24. The system of claim 18, wherein the third sensory input includes a haptic input.

25. The system of claim 18, wherein the third sensory input includes an olfactory input.

26. The system of claim 18, wherein the third sensory input includes a photic input.

27. A system for altering a user's motional response to sensory input from more than one sensory input device, the system comprising:
a current source;
a first sensory input device configured to provide a combined first and second sensory input to a user;
a second sensory input device configured to provide a third sensory input to the user;
a sensor device configured to detect motions associated with the user;
a control unit configured to receive signals from a sensor and receive sensory signals related to the first and second sensory inputs, the control unit generating control signals based on one or more signals and the sensory signals; and electrical contacts configured to contact flesh of the user and deliver a current from a current source through the flesh and directly to the vestibular nerve of the user's vestibular system of the user in response to one or more control signals and the current configured to influence the user to make a predetermined motion if the user is not in the process of making the predetermined motion.

28. The system of claim 27, wherein the first sensory input includes an audio input.

29. The system of claim 27, wherein the first sensory input includes a haptic input.

30. The system of claim 27, wherein the first sensory input includes an olfactory input.

31. The system of claim 27, wherein the first sensory input includes a sensory.

32. The system of claim 27, wherein the third sensory input includes an audio input.

33. The system of claim 27, wherein the third sensory input includes a haptic input.

34. The system of claim 27, wherein the third sensory input includes an olfactory input.

35. The system of claim 27, wherein the third sensory input includes a photic input.

* * * * *